(12) United States Patent
Majeed

(10) Patent No.: US 9,480,330 B2
(45) Date of Patent: Nov. 1, 2016

(54) CLEANING DEVICE

(76) Inventor: Ali Waqar Majeed, Sheffield South (GB)

(*) Notice: Subject to any disclaimer, the term of this patent is extended or adjusted under 35 U.S.C. 154(b) by 352 days.

(21) Appl. No.: 13/821,238

(22) PCT Filed: Sep. 12, 2011

(86) PCT No.: PCT/GB2011/051705
§ 371 (c)(1),
(2), (4) Date: May 28, 2013

(87) PCT Pub. No.: WO2012/038719
PCT Pub. Date: Mar. 29, 2012

(65) Prior Publication Data
US 2013/0276248 A1    Oct. 24, 2013

(30) Foreign Application Priority Data

Sep. 20, 2010  (GB) .................................. 1015632.1
Dec. 16, 2010  (GB) .................................. 1021365.0

(51) Int. Cl.
| | | |
|---|---|---|
| A46B 7/04 | (2006.01) |
| A46B 11/06 | (2006.01) |
| A46B 13/04 | (2006.01) |
| A61B 1/12 | (2006.01) |
| B08B 1/04 | (2006.01) |
| A46B 11/00 | (2006.01) |

(Continued)

(52) U.S. Cl.
CPC .......... *A46B 11/0072* (2013.01); *A46B 5/0095* (2013.01); *A46B 11/06* (2013.01); *A46B 13/04* (2013.01); *A61B 1/122* (2013.01); *A61B 1/125* (2013.01); *A61B 90/70* (2016.02); *B08B 1/008* (2013.01); *B08B 1/04* (2013.01); *B08B 9/00* (2013.01); *A46B 7/042* (2013.01); *A46B 2200/3013* (2013.01); *A61B 2090/701* (2016.02)

(58) Field of Classification Search
CPC .... A46B 5/0095; A46B 13/04; A46B 11/06; A46B 11/0072; A46B 2200/3013; B08B 9/027; B08B 1/04; A61B 2019/343; A61B 1/122; A61B 1/125; A61B 19/34
USPC ............. 15/24, 29, 104.09, 104.095, 104.16, 15/104.2
See application file for complete search history.

(56) References Cited

U.S. PATENT DOCUMENTS

| | | | | |
|---|---|---|---|---|
| 1,247,484 | A | * | 11/1917 | Albrecht ........................... 15/24 |
| 1,468,219 | A | * | 9/1923 | Snazelle et al. ................ 15/103 |

(Continued)

FOREIGN PATENT DOCUMENTS

| | | |
|---|---|---|
| CN | 201188967 Y | 2/2009 |
| CN | 201516015 U | 6/2010 |

(Continued)

*Primary Examiner* — Monica Carter
*Assistant Examiner* — Andrew A Horton
(74) *Attorney, Agent, or Firm* — patenttm.us

(57) ABSTRACT

A cleaning device (10, 110) comprises a body (16, 116), a cleaning arrangement (14, 14), and a driver (18, 118) to effect motion of the cleaning arrangement. The driver is held by the body, and the driver comprises a mounting arrangement (30, 32, 180, 82) to detachably mount the cleaning arrangement on the driver. There is also disclosed a cleaning arrangement (14, 14) for use with a drive arrangement (12, 112) of a cleaning device (10, 110). The cleaning arrangement has a longitudinal main axis and comprising a support (124) extending along the main axis. The cleaning arrangement further includes a brush part (126) on the support, the brush part extending radially outwardly from the support.

16 Claims, 5 Drawing Sheets

(51) Int. Cl.
*A46B 5/00* (2006.01)
*B08B 1/00* (2006.01)
*B08B 9/00* (2006.01)

(56) References Cited

U.S. PATENT DOCUMENTS

| | | | | |
|---|---|---|---|---|
| 1,563,707 | A | * | 12/1925 | Hohl .......................... 192/69.8 |
| 2,911,665 | A | * | 11/1959 | MacKiewicz et al. ......... 15/321 |
| 3,409,924 | A | * | 11/1968 | Slama .............................. 15/24 |
| 3,491,774 | A | * | 1/1970 | Carbone ...................... 132/272 |
| 3,605,154 | A | * | 9/1971 | Dawkins ........................... 15/24 |
| 4,060,870 | A | * | 12/1977 | Cannarella ....................... 15/24 |
| 4,177,532 | A | * | 12/1979 | Azuma ............................. 15/24 |
| 4,619,009 | A | | 10/1986 | Rosenstatter |
| 4,827,551 | A | * | 5/1989 | Maser ................... A61H 13/00 |
| | | | | 15/24 |
| 5,146,642 | A | * | 9/1992 | Mank et al. ...................... 15/24 |
| 5,700,146 | A | * | 12/1997 | Kucar ............................. 433/82 |
| 5,781,955 | A | | 7/1998 | Hendricks |
| 6,062,229 | A | | 5/2000 | Kandratavich et al. |
| 6,253,404 | B1 | * | 7/2001 | Boland et al. ................. 15/22.1 |
| 2002/0152565 | A1 | | 10/2002 | Klupt |
| 2004/0214135 | A1 | | 10/2004 | Ruddle |
| 2008/0230246 | A1 | | 9/2008 | Dollar-Wright |

FOREIGN PATENT DOCUMENTS

| | | |
|---|---|---|
| DE | 202007000839 U | 4/2007 |
| EP | 0254460 A1 | 1/1988 |
| GB | 2382979 A | 6/2003 |
| GB | 2451445 A | 2/2009 |
| JP | 10272097 A | 10/1998 |
| JP | 2000202379 A | 7/2000 |
| JP | 2002-51978 A | 2/2002 |
| JP | 2004-208961 A | 7/2004 |
| JP | 2004290624 A | 10/2004 |
| JP | 2005230496 A | 9/2005 |
| JP | 2007313039 A | 12/2007 |
| JP | 2009183470 A | 8/2009 |

* cited by examiner

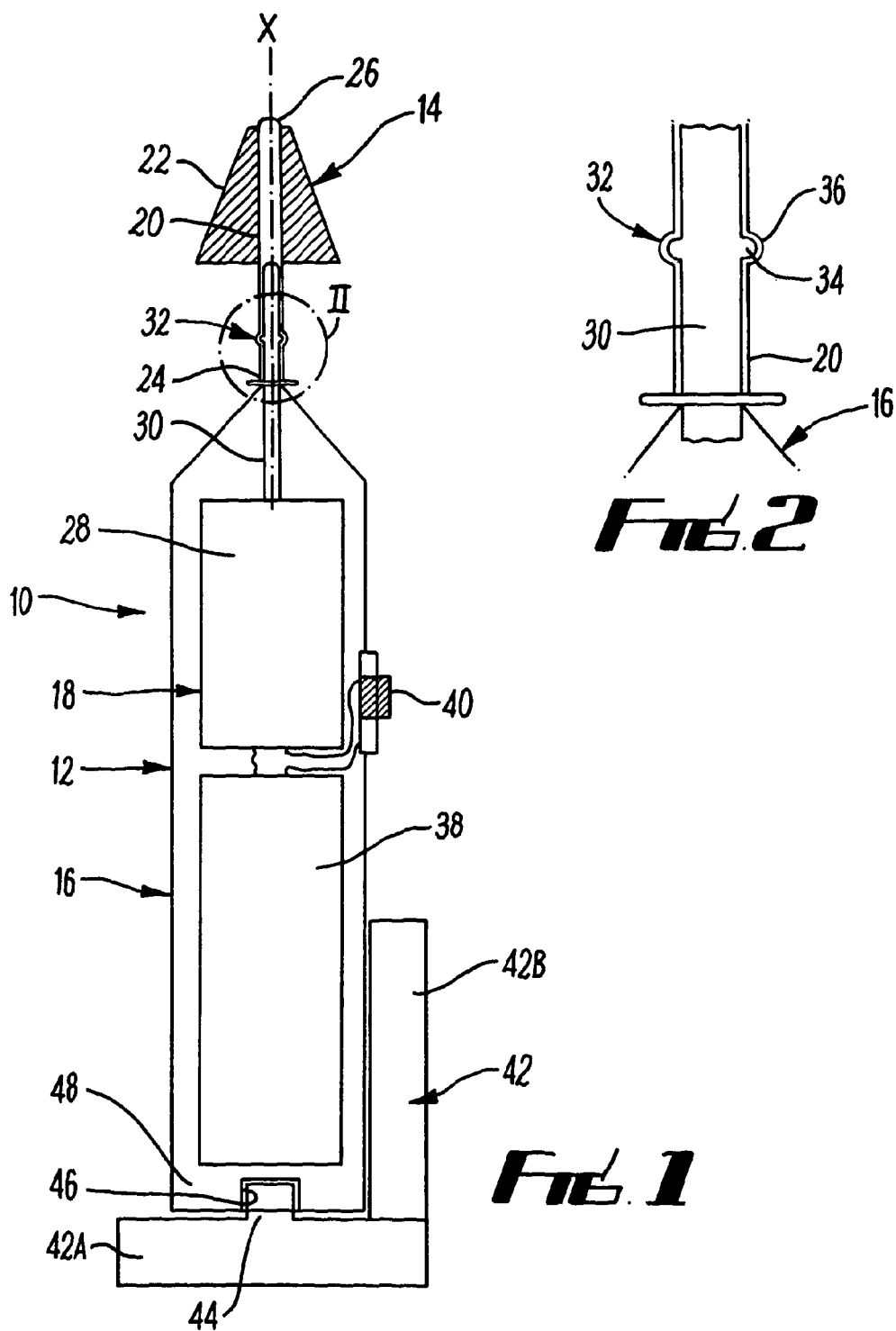

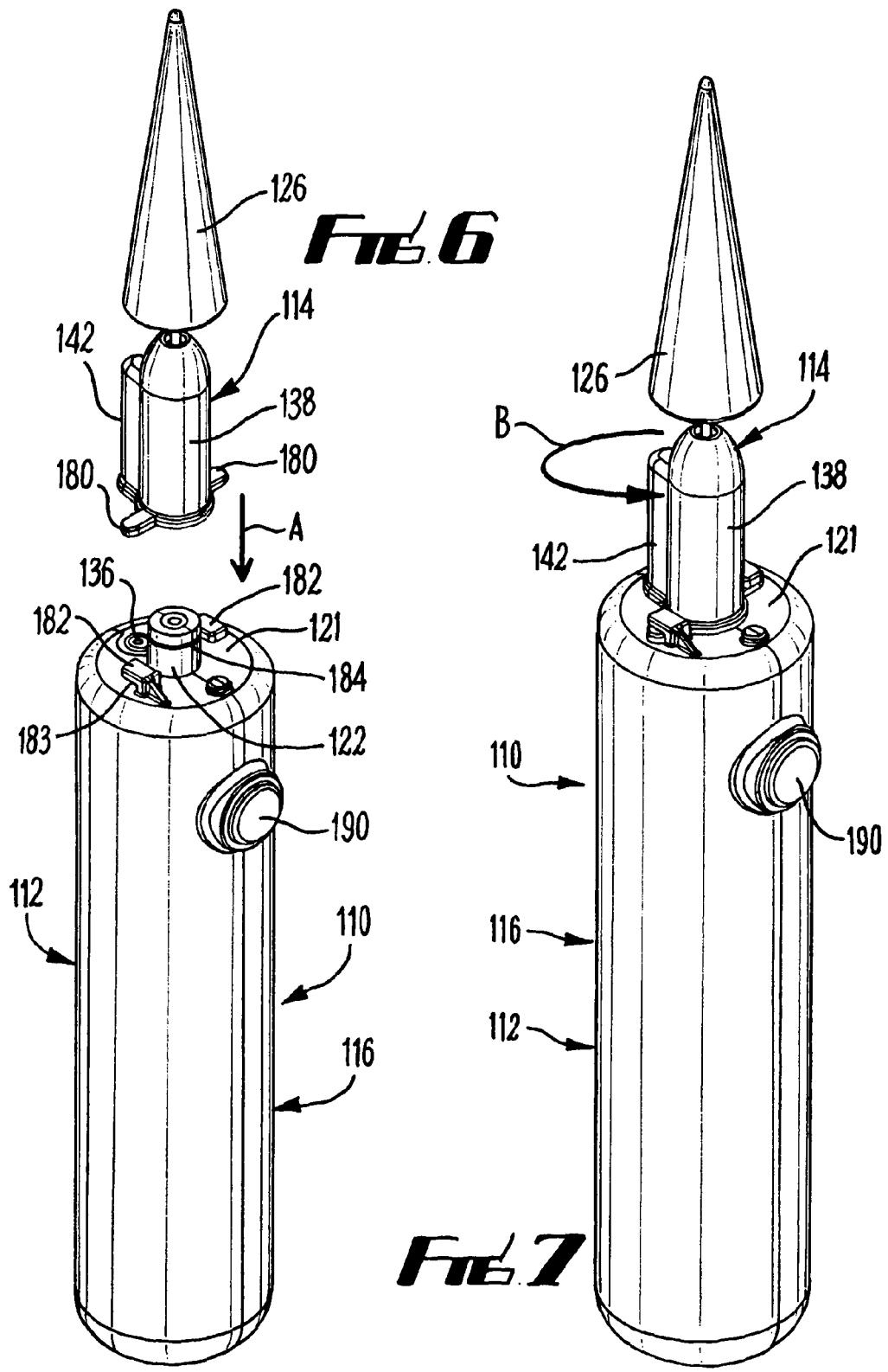

CLEANING DEVICE

This invention relates to cleaning devices. More particularly, but not exclusively, this invention relates to cleaning devices for surgical or medical apparatus. Embodiments of the invention relate to endoscope cleaning devices. This invention also relates to cleaning arrangements for cleaning devices. This invention also relates to drive arrangements for cleaning devices After use of an endoscope, it is passed for cleaning. The initial cleaning stage involves inserting a brush manually into a recess in the endoscope from which the channels lead. This is a time-consuming and dirty operation.

According to one aspect of this invention, there is provided a cleaning device comprising a body, a cleaning arrangement, a driver to effect motion of the cleaning arrangement, the driver being held by the body, wherein the driver comprises a mounting arrangement to detachably mount the cleaning arrangement on the driver.

According to another aspect of this invention, there is provided a drive arrangement for a cleaning device, said drive arrangement comprising a body, a driver to effect motion of a cleaning arrangement, the driver being held by the body, wherein the driver comprises a mounting arrangement to detachably mount the cleaning arrangement on the driver.

The cleaning device may comprise a cleaning device for surgical or medical apparatus. The cleaning device may comprise an endoscope cleaning device.

A plurality of cleaning arrangements may be provided, wherein a selected one of the cleaning arrangements may be mountable on the driver.

The motion of the cleaning arrangement effected by the driver may be rotary motion. In one embodiment, the motion of the cleaning arrangement effected by the driver may be an oscillatory motion. The oscillatory motion may be rotary and/or linear. The linear motion may be linear motion in one, two or three orthogonal dimensions.

The linear motion may be an up and down motion, and/or a side to side motion, and/or a forwards and backwards motion.

The, or each, cleaning arrangement may comprise a brush. The, or each, brush may comprise a support and a brush part on the support.

The support may be elongate. The brush part may extend along the support. The brush part may extend radially from the support. The brush part may be generally conical, or frustoconical, in configuration.

According to a further aspect of this invention, there is provided a cleaning arrangement for a cleaning device, the cleaning arrangement comprising a support and a brush part on the support, the brush part being generally conical, or frustoconical, in configuration.

The cleaning arrangement may be for use with a cleaning device for surgical or medical apparatus. The cleaning arrangement may be for use with an endoscope cleaning device.

The elongate support may comprise a proximal end and a distal end. The brush part may be provided at or adjacent the distal end of the support.

The brush part may taper outwardly from the distal end towards the proximal end of the support.

In a first embodiment, the support may include a securing formation to secure the cleaning arrangement to the drive arrangement. The securing formation may be provided at the proximal end of the support. The securing formation may comprise a recess defined in the support. The recess may be elongate. The support may be tubular.

In the first embodiment, the mounting arrangement may include a mounting member upon which the cleaning arrangement can be mounted. The mounting member may be elongate, and may be configured to co-operate with the securing formation to secure the cleaning arrangement to the mounting member. The mounting member may be receivable by the recess in the support. The mounting arrangement may have a longitudinal main axis, and the cleaning arrangement may be rotatable about said longitudinal main axis. In the first embodiment, the mounting member may be configured to transmit torque from the driver to the cleaning arrangement.

The driver may include a driving mechanism, which may comprise a motor. The aforesaid longitudinal main axis may be the main axis of the mounting member. The mounting member may constitute an elongate shaft having said longitudinal main axis. In the first embodiment, the driving mechanism may be configured to drive the mounting member with oscillating motion on the aforesaid shaft.

In a second embodiment, the mounting arrangement may comprise a transmission member to transmit torque from the driver to the cleaning arrangement. The transmission member may have a first co-operating region to co-operate with the support, and a second co-operating region to co-operate with the driving mechanism. The transmission member may be elongate and the first and second co-operating regions may be first and second opposite end regions of the transmission member.

An attaching member may be provided to attach the support to the mounting arrangement. The attaching member may be configured to co-operate with the transmission member to attach the support to the mounting arrangement. Desirably, the attaching member is configured to co-operate with the first co-operating region of the transmission member to attach the support to the mounting member.

In the second embodiment, the cleaning arrangement may include a housing through which the support extends. The cleaning arrangement may comprise a locating member to locate the support in the housing. The support may extend through the locating member, and the locating member may have an edge to engage the housing. The locating member may comprise a disc with a hole through which the support extends.

The first co-operating region of the transmission member may define a recess, and the attaching member may be received in the recess to attach the support to the transmission member.

The support may be elongate and the attaching member may be provided at a proximal end of the support.

The mounting arrangement and the support may include co-operating fastening formations to fasten the cleaning arrangement to the mounting member.

In the first embodiment, the co-operating fastening formations may comprise a projection on one of the support and the mounting member, and an indent on the other of the support and the mounting member. The projection may be provided on the mounting member, and the recess may be defined in the support. The projection and the recess may extend around the support or the mounting member.

The co-operating fastening formations may be provided on the housing and on the body.

In the second embodiment, the co-operating fastening formations may comprise a bayonet fixing to fasten the cleaning arrangement to the mounting arrangement.

The co-operating fastening formations may comprise at least one receiving member on one of the housing and the body, and at least one insertion member on the other of the housing and the body, the insertion member being configured to be received by the receiving member. The co-operating fastening formations may comprise two receiving members and two insertion members arranged opposite each other on the body and the housing respectively. The, or each, receiving member may be substantially L shaped.

In the second embodiment, the body may comprise a main part and a lug on the main part. The housing may be configured to receive the lug to locate the cleaning arrangement on the body.

The housing may comprise a main portion which can receive the lug, and the housing may further include a subsidiary portion on the main portion.

The motor may be an electric motor, and the driver may include means for providing electricity, such as a battery, or connection means to connect the cleaning device to a supply of electricity, such as a mains supply of electricity.

Actuating means may be provided on the body to actuate the driver. The actuating means may comprise a switch or button to actuate the driver.

A fluid delivery arrangement may be provided to deliver fluid to the cleaning arrangement. in the first embodiment, the fluid delivery member may comprise a conduit, such as a tube, which may extend along the body. The delivery arrangement may be connectable to a supply of fluid. The fluid delivered by the delivery arrangement may comprise a cleaning fluid. The fluid may comprise water.

In the second embodiment, the fluid delivery arrangement may comprise a fluid feed conduit to feed fluid to the cleaning arrangement. The fluid feed conduit may be elongate, such as in the form of a tube. The fluid feed conduit may be disposed within the body. The body may define a feed aperture to feed fluid to the cleaning arrangement.

The housing may define a fluid channel to direct fluid onto the brush part. The housing may define an opening to allow fluid communication between the fluid channel and the fluid delivery arrangement. The opening may allow the fluid channel to receive fluid from the fluid delivery conduit when the opening is aligned with the fluid feed aperture. The opening may be offset from the support. The opening may be offset from the longitudinal main axis of the mounting arrangement.

The fluid channel may comprise a main channel region, through which the support can extend. The main portion of the housing may comprise the main channel region of the fluid channel.

The fluid channel may further include a connecting channel region to connect the main channel to the fluid feed conduit. The connecting channel region may be arranged adjacent the main channel region. The connecting channel region of the fluid channel may comprise the subsidiary portion of the housing.

The housing may define a first opening to effect fluid communication between the fluid feed conduit and the connecting channel region. When the cleaning arrangement is mounted on the body, the first opening in the housing may be aligned with the feed aperture in the body.

The cleaning arrangement can be disposed on the body and may be movable relative to the body to align the opening with the fluid feed aperture. The cleaning arrangement may be mountable on the body, and may thereafter be movable relative to the body so that the, or each, insertion member is received by the, or a respective, receiving member. The cleaning arrangement may be movable by being rotatable relative to the body.

The housing may define a second opening to effect fluid communication between the connecting channel region and the main channel region.

The housing may comprise a wall to separate the main channel region from the connecting channel region. The wall may define the aforesaid second opening.

The housing may further include a delivery aperture through which cleaning fluid can pass from the housing to the brush part of the cleaning arrangement.

The actuating means may be configured to actuate the supply of fluid to supply said fluid to the fluid delivery arrangement. The actuating means may be connectable, such as by an electric cable or by wireless connection to a pump for pumping the fluid to the fluid delivery arrangement. The switch or button for actuating the driver may also be arranged to actuate the fluid delivery arrangement.

A control assembly may be provided to control said supply of fluid. The control assembly may comprise the pump. The control assembly may comprise a control box in which the pump is housed.

According to another aspect of this invention, there is provided the use of a cleaning device in cleaning surgical or medical apparatus, the cleaning device being as described above.

According to a further aspect of this invention, there is provided a method of cleaning a surgical or medical apparatus, providing a cleaning device as described above and using the aforesaid cleaning device to effect cleaning of the surgical or medical apparatus. The method may comprise a method of cleaning an endoscope.

The method may comprise mounting the cleaning arrangement, or a selected one of the cleaning arrangements, on the driver and actuating the driver to effect rotation of the cleaning arrangement.

After the surgical or medical apparatus has been cleaned, the method may comprise detaching the cleaning arrangement from the driver and disposing of the cleaning arrangement.

Embodiments of the invention will now be described by way of example only, with reference to the accompanying drawings, in which:

FIG. 1 is a sectional side view of a cleaning device;

FIG. 2 is a close up view of the region marked II in FIG. 1;

FIG. 6 is a perspective view of the embodiment shown in FIG. 4, showing a first step of mounting a cleaning arrangement on a drive arrangement;

FIG. 7 is a perspective view of the embodiment shown in FIG. 5 showing a second step of mounting the cleaning arrangement on the drive arrangement.

Figure 3:
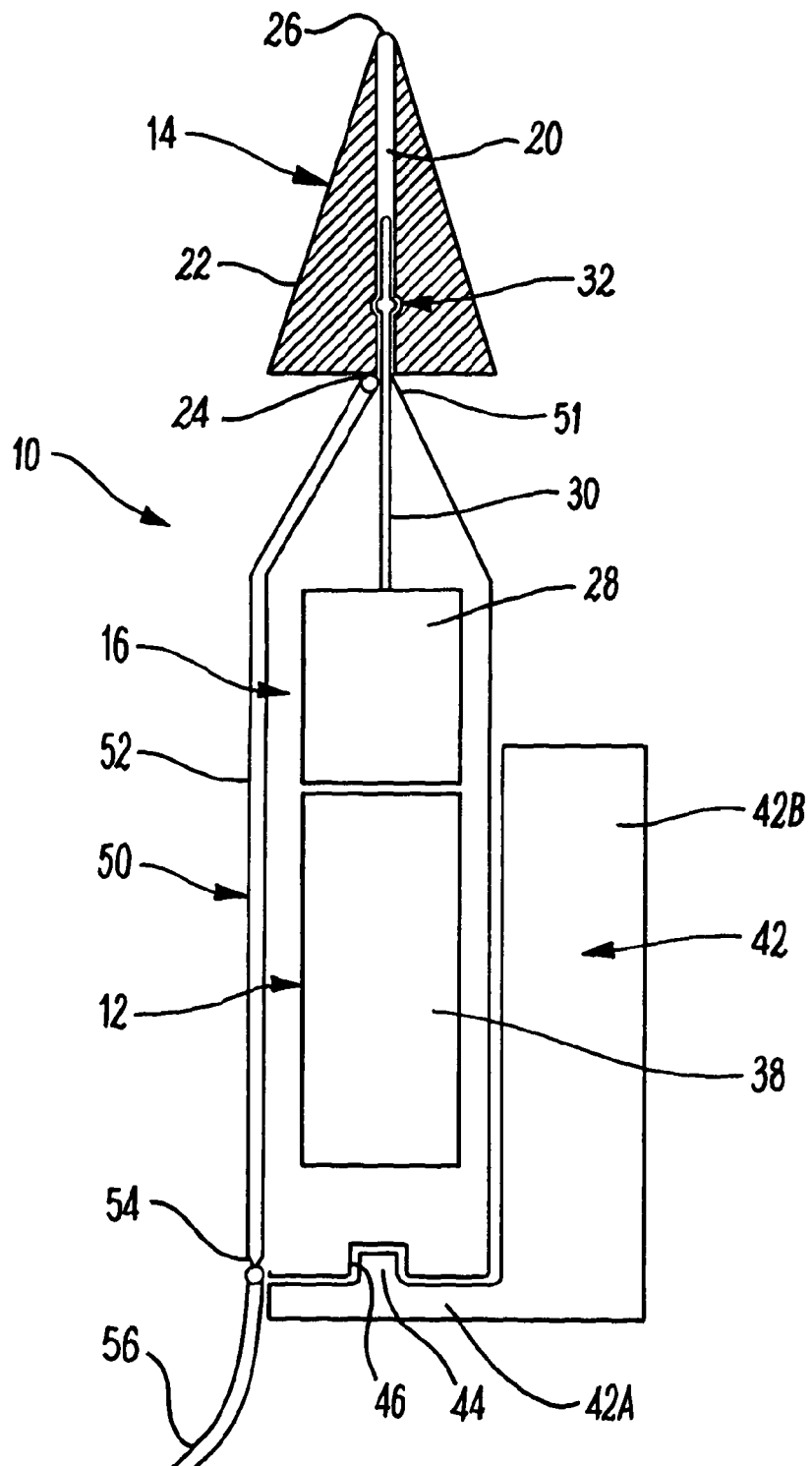
FIG. 3 is a sectional side view of a further embodiment of a cleaning device.
Figure 4:
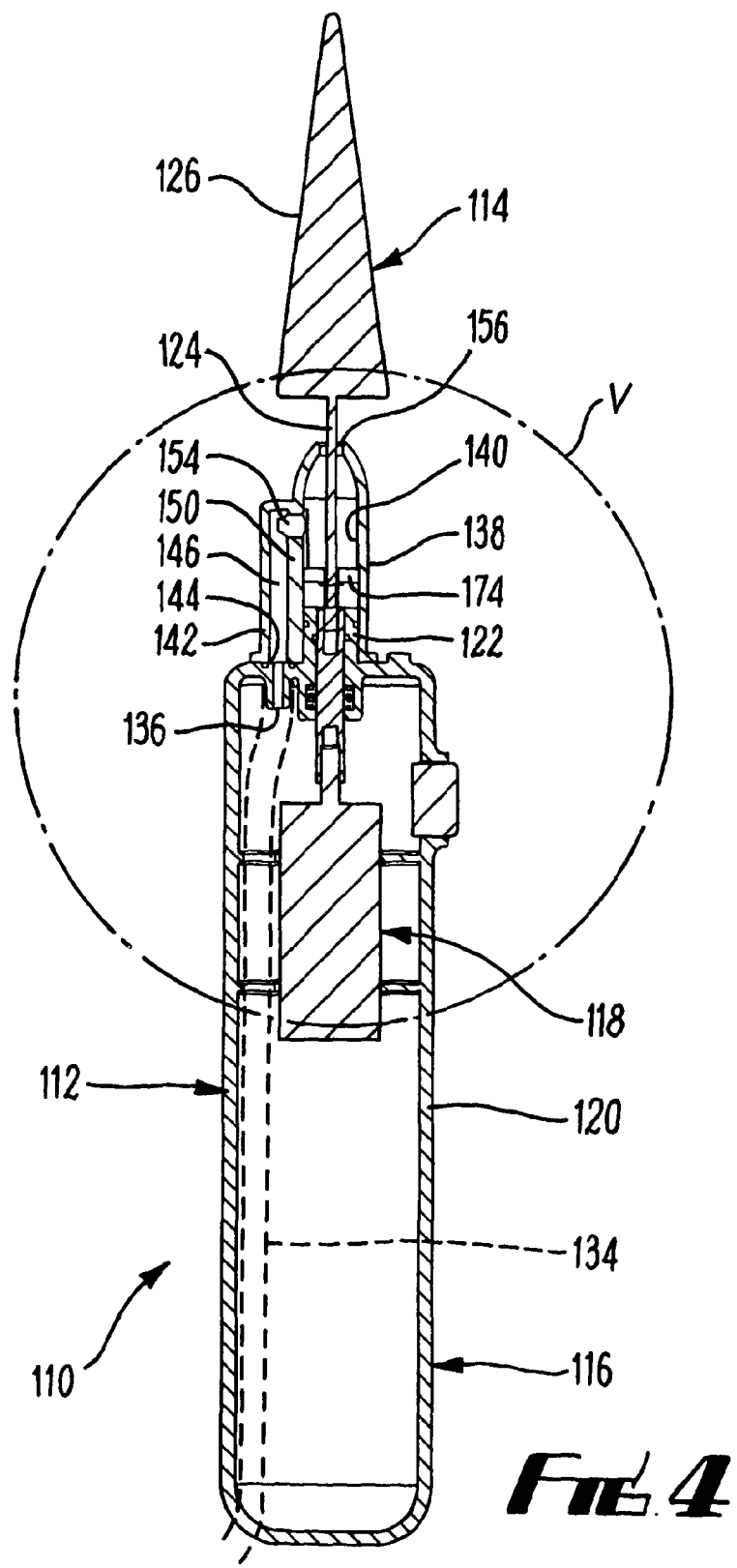
FIG. 4 is a sectional side view of a second embodiment of a cleaning device.
Figure 5:
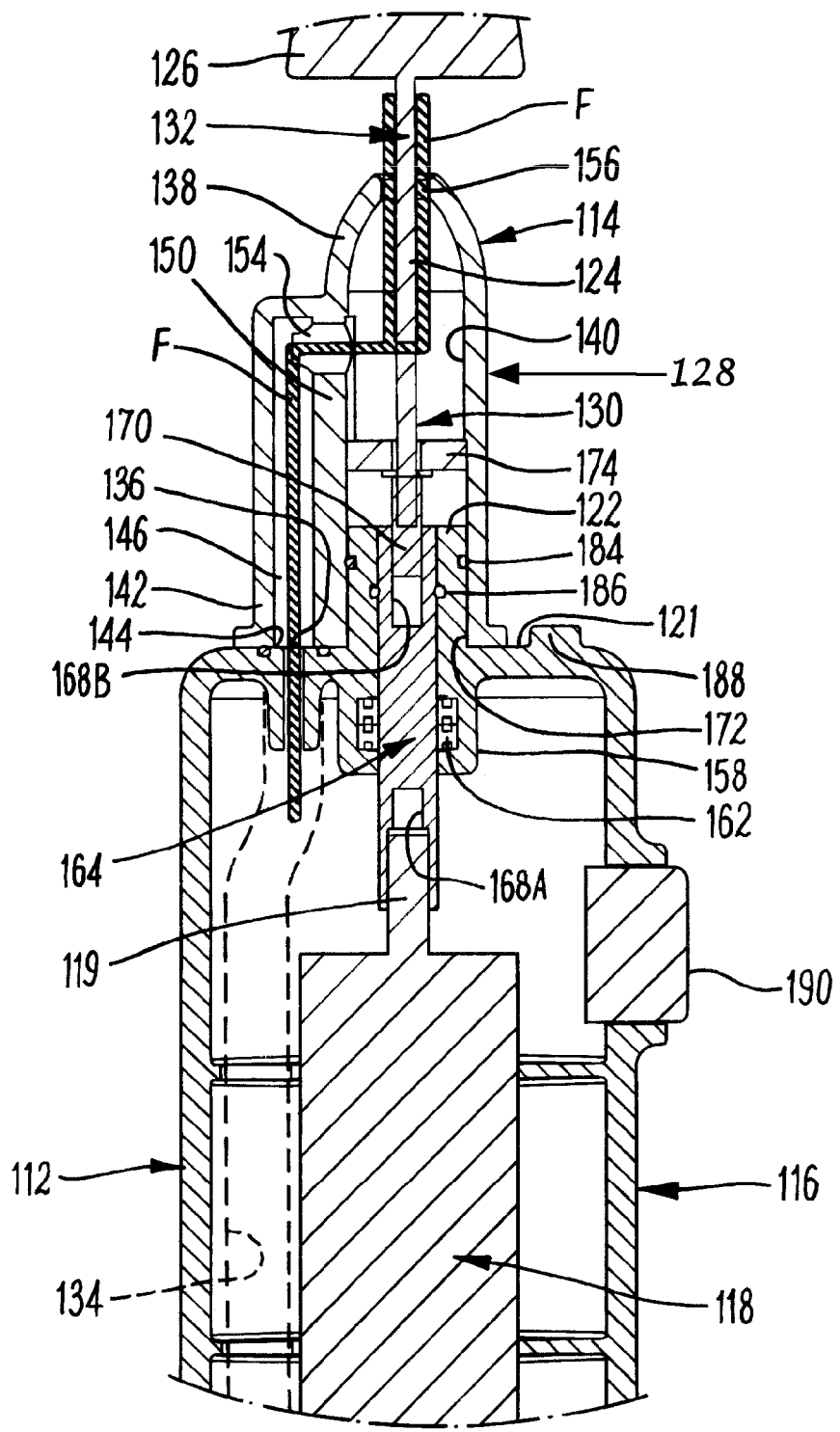
FIG. 5 is a close up view of the region marked V in FIG. 4

FIG. 1 shows an endoscope cleaning device 10 for cleaning the valve housings of a soiled endoscope (not shown) after use. The endoscope cleaning device 10 comprises a drive arrangement 12 on which a cleaning arrangement 14 is detachably mounted. The drive arrangement 12 comprises a body 16 and a driver 18 held by the body 16.

The cleaning arrangement 12 is one of a plurality of cleaning arrangements 12, to allow the user to replace a soiled cleaning arrangement 12 with a clean further cleaning arrangement 12 for further cleaning, or to select a different size cleaning arrangement 12 for cleaning different regions of the same endoscope, or a different endoscope.

The cleaning arrangement 14 comprises an elongate tubular support 20 and a frustoconical brush part 22. The elongate support 20 has a proximal end region 24 and a distal end region 26. The brush part 22 is provided at the distal end region 26 and tapers outwardly from the distal end region 26 towards the proximal end region 24. As can be seen from the drawing, the brush part 22 occupies approximately half of the length of the elongate support 20.

The driver 18 comprises a drive mechanism in the form of an electric motor 28 and a mounting arrangement comprising an elongate mounting member in the form of a shaft 30 extending from the electric motor 28.

The shaft 30 has a longitudinal axis X and is rotatable by the motor 28 about its longitudinal axis X.

The shaft 30 and the tubular support 20 together include co-operating fastening formations 32 which act to fasten the cleaning arrangement 16 on the shaft 28. As shown more clearly in FIG. 2, the co-operating fastening formations 32 comprise a radially extending projection 34 on the shaft 30, and a radially extending indent 36 defined on the inside of the tubular support 20. When the cleaning arrangement 14 is mounted on the shaft 30, the radially extending indent 36 receives the radial projection 34.

The electric motor 28 is powered by a battery 38 held in the body 16 beneath the electric motor 28.

A switch 40 is electrically connected between the battery 38 and the motor 28 and is operable to electrically connect the electric motor 28 to the battery 38 as desired.

The battery 38 may be a rechargeable battery, which can be recharged by a charger 42 which can be connected to a mains supply of electricity. In order to hold the drive arrangement 12 on the charger 42, the charger 42 includes a base portion 42A and an upright portion 42B. A projection 44 extends from the base portion 42A, and is received in a recess 46 at a proximal end 48 of the body 16. The battery 38 is charged by the charger 42 by induction. As can be seen, the charger 42 also acts as a stand for the endoscope cleaning device 10.

In operation, the user may mount a selected one of the cleaning arrangements 16 on the shaft 30, as described above.

When the cleaning arrangement 14 is mounted on the shaft 30, the button 40 can be depressed to rotate the cleaning arrangement 14 about the longitudinal axis X of the shaft 30. If desired, a supply of water may be provided to enhance the cleaning of the endoscope 10.

The motor 28 may drive the cleaning arrangement 14 in an oscillatory motion. The oscillatory motion of the cleaning arrangement 13 may be rotary and/or linear. The linear motion may be an up and down motion, and/or a side to side motion, and/or a forwards and backwards motion.

The user grips the endoscope cleaning device 10 around the body 16 and inserts the rotating cleaning arrangement 14 into a recess of the endoscope to be cleaned. The rotation of the cleaning arrangement 14 then cleans the recess in the endoscope.

After the recess in the endoscope has been cleaned, the cleaning arrangement 14 is detached from the shaft 30, and then disposed of in a suitable receptacle.

The user may then mount a further cleaning arrangement 14 on the shaft 30 for cleaning of a further endoscope, or a further recess in the same endoscope. Alternatively, if the user has completed his or her work, the endoscope cleaning device 10 can be returned to the charger 42 for charging purposes.

Various modifications can be made without departing from the scope of the invention. For example, the indent and projection forming the co-operating fastening formations 32 could be the opposite way round, i.e. the indent could be provided in the shaft 30, and the projection may extend radially inwardly from the tubular support 20, to be received in the indent defined in the shaft 30.

A further embodiment of the endoscope cleaning device 10 is shown in FIG. 3, which comprises many of the features of the endoscope cleaning device 10 shown in FIGS. 1 and 2, and the features shown in FIG. 3 have been designated with the same reference numerals as the corresponding features in FIGS. 1 and 2.

The endoscope cleaning device 10 shown in FIG. 3 differs from the endoscope cleaning device shown in FIGS. 1 and 2, in that it comprises a fluid delivery arrangement 50 for delivering a cleaning fluid in the form of water to a distal end 51 of the body 16 and to the cleaning arrangement 14. The fluid delivery arrangement 50 comprises a conduit in the form of a tube 52 extending along the length of the body 16 from the proximal end 48 to the distal end 51.

The fluid delivery arrangement 50 further includes a connector 54 on the tube 52 at the proximal end 48 of the body 16 to connect the tube 52 to a supply pipe 56 for supplying the fluid to the fluid delivery arrangement 50. The supply pipe 56 is connected to a pump (not shown), which in turn is connected to a supply of water.

The pump is mounted in a suitable control box, which may be used to house components for use with other cleaning apparatus.

For reasons of clarity the button 40 is not shown in FIG. 3, but it is present in the embodiment shown in FIG. 3, and is connected via suitable electric wiring along the supply pipe 56 to the pump. Depressing the button 40 actuates not only the motor 28, but also the pump to supply water to the fluid delivery arrangement 50 and, hence, to the cleaning arrangement 14.

The cleaning arrangement 14 shown in FIG. 3 differs from the cleaning member 14 shown in FIG. 1, in that the brush part 22 of the cleaning arrangement 14 shown in FIG. 3 is substantially conical in configuration, and extends substantially wholly along the length of the elongate support 20.

FIGS. 4 to 7 show a second embodiment of an endoscope cleaning device generally designated 110. The endoscope cleaning device 110 comprises a drive arrangement 112 on which a cleaning arrangement 114 is detachably mounted.

The drive arrangement 112 comprises a body 116 and a driver 118 having a shaft 119 held within the body. The driver 118 is in the form of an electric motor.

The body 116 comprises a main part 120 providing an engagement face 121 and a cylindrical projection in the form of a lug 122 on the engagement face 121 of the main part 120. The lug 122 locates the cleaning arrangement on the body 116. The engagement face 121 is engaged by the cleaning arrangement 114 when the cleaning arrangement 114 is mounted on the body 116.

The cleaning arrangement 114 comprises an elongate support 124 on which a conical brush part 126 is provided. The elongate support 124 may be in the form of a further shaft.

The cleaning arrangement 114 further includes a housing 128 in which the elongate support 124 is received. The elongate support 124 has a proximal end region 130 received in the housing 128 and a distal end region 132 extending from the housing 128. The brush part 126 is provided on the distal end region 132 of the elongate support 124.

A fluid supply conduit 134 (shown in broken lines in FIGS. 4 and 5) is provided within the body 116. The fluid supply conduit 134 can be connected to a mains supply of a cleaning fluid (not shown) such as water. The engagement face 121 defines a fluid supply aperture 136. An end of the fluid supply conduit 134 is connected to the body 116 at the fluid supply conduit 134 so that fluid can be supplied from the fluid supply conduit 134 via the fluid supply aperture 136.

The housing 128 comprises a main portion 138 defining a main fluid channel region 140. The housing 128 also has a subsidiary portion 142 provided on the main portion 138. The subsidiary portion 142 defines a fluid receiving opening 144 and a connecting channel region 146 to connect the fluid conduit 134 in fluid communication with the main channel region 140. The fluid receiving opening 144 is offset from the elongate support 124.

A wall 150 is provided within the housing 128 and separates the main fluid channel region 140 from the connecting fluid channel region 146. The wall 150 defines a communication opening 154 to allow fluid communication between the connecting channel region 146 and the main channel region 140.

When the cleaning arrangement 114 is mounted on the drive arrangement 112 in the manner described in more detail below, the fluid receiving opening 144 is aligned with the fluid supply aperture 136 so that fluid passing along the fluid supply conduit 134 can pass into the connecting channel region 146 via the fluid supply aperture 136 and the fluid receiving opening 144. The fluid receiving opening 114 and the connecting channel region 146 are offset from the elongate support 124 and the shaft 30. The fluid flows from the connecting channel region 146 in to the main fluid channel 140 via the communication opening 154 in the wall 150.

The housing 128 defines a fluid delivery aperture 156 through which the elongate support 124 extends. A gap is defined between the elongate support 124 and the edge of the fluid delivery aperture 156. The gap allows fluid F in the main channel region 140 to flow out of the housing 128 on to the brush part 126.

The main part 120 of the body 116 includes a bearing holding member 158 defining a bore 160. The bore 160 extends through the bearing holding member 158 and through the lug 122.

An elongate transmission member 164 extends from the shaft 119 through bore 160 in the bearing holding member 158 and the lug 122. Bearings 162 are provided in the bearing holding member 158 and the transmission member 164 is journalled within the bearings 162.

The transmission member 164 has recesses 168A, 168B defined in the opposite ends thereof. The shaft 119 is a friction fit within the recess 168A in the transmission member 164 so that rotation of the shaft 119 about its main axis is transmitted to the transmission member 164.

The elongate support 124 has an attaching member 170 mounted on the proximal end region 130 thereof. The attaching member 170 is received in the recess 168B at the opposite end of the transmission member 164 and is a friction fit therein. Thus, when the driver 118 is operated, torque therefrom is transmitted by the transmission member 164 to the elongate support 124.

The main portion 138 of the housing 128 defines a lug receiving opening 172 to receive the lug 122 therein. As the lug 122 is received within the lug receiving opening 172, the attaching member 170 is received in the recess 168B in the end region of the transmission member 164, thereby connecting the transmission member 164 to the elongate support 124.

A locating member, in the form of a locating disc 174 is provided to locate the elongate support 124 in the housing 128. The elongate support 124 extends through the locating disc 174. The circumferential edge of the locating disc 174 engages the main portion 138 of the housing 128 to provide the location of the elongate support 124 therein.

Referring to FIGS. 6 and 7, a mounting arrangement in the form of co-operating fastening formations are provided on the housing 128 and on the engagement face 121 of the main part 120. The co-operating fastening formations are in the form of a bayonet fixing on the engagement face 121 of the body 116 and on the housing 128. The bayonet fixing comprises a pair of radially outwardly extending insertion members 180 arranged opposite each other on the housing 128, with the housing 128 disposed between the insertion members 180. The bayonet fixing also include a pair of L-shaped receiving members 182 on the engagement face 121 of the body 116. Each L-shaped receiving member 182 defines a gap 183 between the receiving member 182 and the engagement face 121 in which a respective one of the insertion members 180 can be received, thereby securing the cleaning arrangement 114 to the drive arrangement 112.

The lug 122 has two sealing members in the form of O-rings 184, 186 thereon. The O-ring 184 is provided externally of the lug 122, being received in a groove on the external surface of the lug 122. The O-ring 184 is provided to create a seal between the lug 122 and the housing 128 of the cleaning arrangement 114. The other O-ring 186 is provided internally of the lug 122 to create a seal between the lug 122 and the transmission member 164.

The cleaning arrangement 114 is secured to the body 116 by the engagement of the insertion members 180 in the gap 183 between the L-shaped receiving members 182 and the engagement face 121 of the body 116. When the cleaning arrangement 114 is so positioned on the body 116, the fluid receiving opening 144 defined by the subsidiary portion 142 of the housing 128 is aligned with the fluid supply aperture 136 in the engagement face 121.

In order to mount the cleaning arrangement 114 on the engagement face 121 of the body 116, the cleaning arrangement 114 first engages the engagement face 121 as shown by the arrow A in FIG. 6. The cleaning arrangement 114 is then rotated as indicated by the arrow B in FIG. 7 so that the insertion members 180 are received in the gaps 183 between the L-shaped receiving members 182 and the engagement face 121.

A stud 188 is provided on the engagement face 121 of the body 116 to prevent the cleaning arrangement 114 being mounted thereon in an incorrect orientation.

An operating button 190 is provided on the body 116, and is connected electrically to the driver 118. The drive arrangement may include a battery (not shown), such as a rechargeable battery, or it may be connected by electric cables to a main supply of electricity. Depression of the operating button 190 causes the driver 118 to operate, thereby rotating the elongate support 124 and the brush part 126. The elongate support 124 rotates relative to the locating disc 174.

The operating button 190 can also be electrically connected to a valve for controlling the flow of cleaning fluid passing through the fluid supply conduit 134. When the button 190 is depressed, the driver 118 is operated and the valve is opened so that cleaning fluid is supplied to the cleaning arrangement 114 when the brush part 126 is rotated.

There are thus described embodiments of an endoscope cleaning device which can be used to effect initial cleaning of parts of an endoscope, such as the valve housings. The above described embodiments are more hygienic and provide a simpler way of effecting such cleaning than known methods.

The invention claimed is:

1. A cleaning arrangement for use with a drive arrangement of a cleaning device, the cleaning arrangement having a longitudinal main axis and comprising a support extending along the main axis, and the cleaning arrangement further including a brush part on the support, and a housing through which the support extends, the brush part extending radially outwardly from the support, wherein the housing defines a fluid channel to direct fluid onto the brush part, the housing comprising a main housing portion defining a main channel region extending along the main axis, and a subsidiary housing portion defining a connecting channel region offset from the main channel region, said offset being in a direction transverse to the main axis, the connecting channel region being configured to connect the main channel to a fluid feed conduit in the drive arrangement, wherein fluid is allowed to flow from the connecting channel region to the main channel region, wherein a gap is defined between the support and an edge of a fluid delivery aperture, the gap allowing fluid to flow out of the main channel region and onto the brush part.

2. A cleaning arrangement according to claim 1, wherein the housing defines a lug receiving opening to receive a lug on the drive arrangement.

3. A cleaning arrangement according to claim 1, wherein the housing defines an opening for the fluid channel to receive fluid from the fluid feed conduit in the drive arrangement when the opening is aligned with the fluid feed conduit.

4. A cleaning arrangement according to claim 1, wherein the connecting channel region is arranged adjacent the main channel region.

5. A cleaning arrangement according to claim 1, wherein the housing defines a first opening to effect fluid communication between the connecting channel region and the fluid feed conduit in the drive arrangement, and the housing defines a second opening to effect fluid communication between the connecting channel region and the main channel region.

6. A cleaning arrangement according to claim 5, wherein the housing comprises a wall to separate the main channel region from the connecting channel region, the wall defining the aforesaid second opening.

7. A cleaning arrangement according to claim 1, wherein the housing further defines a delivery aperture through which cleaning fluid can pass from the housing to the brush part of the cleaning arrangement.

8. A cleaning arrangement according to claim 1, having a locating member to locate the support in the housing, the support extending through the locating member, and the locating member having an edge to engage the housing.

9. A cleaning arrangement according to claim 8, wherein the locating member comprises a disc defining a hole through which the support extends.

10. A cleaning arrangement according to claim 1, wherein the brush part is generally conical or frustoconical in configuration.

11. A cleaning arrangement according to claim 1, for use as part of an endoscope cleaning device.

12. A cleaning arrangement according to claim 1, including fastening formations co-operable with corresponding fastening formations on the drive arrangement to fasten the cleaning arrangement to the drive arrangement.

13. A cleaning arrangement according to claim 12, wherein the fastening formation comprises an insertion member which can be received by a receiving member on the drive arrangement.

14. A cleaning arrangement according to claim 12, wherein the fastening formations comprise a part of a bayonet fixing.

15. A cleaning device comprising a body, a cleaning arrangement having fastening formations, a driver to effect motion of the cleaning arrangement, the driver being held by the body, wherein the driver comprises a mounting arrangement to detachably mount the cleaning arrangement on the driver, the mounting arrangement comprising further fastening formations, said further fastening formations co-operating with the fastening formations on the cleaning arrangement to fasten the cleaning arrangement to the driver, wherein the cleaning arrangement has a longitudinal axis and comprises a brush, having an elongate support mountable on the driver, and the cleaning arrangement further including a brush part on the support extending radially outwardly therefrom, the brush part and the support extending along the longitudinal axis, and the cleaning arrangement further includes a housing through which the support extends, wherein the housing defines a fluid channel to direct fluid onto the brush part, the housing comprising a main housing portion defining a main channel region extending along the main axis, and a subsidiary housing portion defining a connecting channel region offset from the main channel region, said offset being in a direction transverse to the main axis, the connecting channel region being configured to connect the main channel to a fluid feed conduit in the drive arrangement and the cleaning device further comprising a fluid delivery arrangement to deliver fluid to the cleaning arrangement, the fluid delivery arrangement comprising a fluid delivery conduit which extends along the body, wherein fluid is allowed to flow from the connecting channel region to the main channel region, wherein a gap is defined between the support and an edge of a fluid delivery aperture, the gap allowing fluid to flow out of the main channel region and onto the brush part.

16. A cleaning device according to claim 15, wherein the body comprises a main part and a cylindrically projecting lug on the main part, and the housing can receive the cylindrically projecting lug to hold the cleaning arrangement on the body, and mount the cleaning arrangement on the driver.

* * * * *